(12) United States Patent
Bogaart et al.

(10) Patent No.: US 10,042,260 B2
(45) Date of Patent: Aug. 7, 2018

(54) DEVICE FOR MONITORING A RADIATION SOURCE, RADIATION SOURCE, METHOD OF MONITORING A RADIATION SOURCE, DEVICE MANUFACTURING METHOD

(71) Applicant: ASML Netherlands B.V., Veldhoven (NL)

(72) Inventors: Erik Willem Bogaart, Someren (NL); Chuangxin Zhao, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/508,543

(22) PCT Filed: Aug. 11, 2015

(86) PCT No.: PCT/EP2015/068466
§ 371 (c)(1),
(2) Date: Mar. 3, 2017

(87) PCT Pub. No.: WO2016/037786
PCT Pub. Date: Mar. 17, 2016

(65) Prior Publication Data
US 2017/0307978 A1 Oct. 26, 2017

(30) Foreign Application Priority Data
Sep. 11, 2014 (EP) .................................. 14184445

(51) Int. Cl.
*G01N 27/22* (2006.01)
*G01N 27/00* (2006.01)
(Continued)

(52) U.S. Cl.
CPC ............... *G03F 7/20* (2013.01); *G01N 27/22* (2013.01); *G03F 7/70033* (2013.01); *G03F 7/7085* (2013.01); *H05G 2/001* (2013.01)

(58) Field of Classification Search
USPC ........ 361/271, 278, 503, 523, 524; 324/658, 324/686
See application file for complete search history.

(56) References Cited

U.S. PATENT DOCUMENTS 5,767,687 A 6/1998 Geist
6,542,350 B1 * 4/2003 Rogers .............. A61M 5/14593
361/278
(Continued)

FOREIGN PATENT DOCUMENTS

EP 0 317 871 A2 5/1989
EP 0 924 492 A1 6/1999
(Continued)

OTHER PUBLICATIONS

International Search Report directed to related International Patent Application No. PCT/EP2015/068466, dated Nov. 13, 2015; 4 pages.
(Continued)

*Primary Examiner* — Bernard Souw
(74) *Attorney, Agent, or Firm* — Sterne, Kessler, Goldstein & Fox P.L.L.C.

(57) ABSTRACT

Capacitive measurements for monitoring vapor or deposits from a vapor in a radiation source for a lithography apparatus. The measurements may be used to control operation of the radiation source. In one particular arrangement measurements from a plurality of capacitors are used to distinguish between changes in capacitance caused by the vapor and changes in capacitance caused by deposits from the vapor.

20 Claims, 8 Drawing Sheets

(51) Int. Cl.
*G03F 7/20* (2006.01)
*H05G 2/00* (2006.01)

(56) References Cited

U.S. PATENT DOCUMENTS

| | | | |
|---|---|---|---|
| 2005/0100475 A1 | 5/2005 | Centanni | |
| 2005/0225308 A1* | 10/2005 | Orvek | G01N 15/0656 |
| | | | 324/71.4 |
| 2005/0269529 A1* | 12/2005 | Ershov | B82Y 10/00 |
| | | | 250/504 R |
| 2006/0163500 A1* | 7/2006 | Inoue | B82Y 10/00 |
| | | | 250/493.1 |
| 2008/0124820 A1* | 5/2008 | Levinson | G03F 7/707 |
| | | | 438/17 |
| 2009/0021270 A1* | 1/2009 | Bandholz | G01N 27/223 |
| | | | 324/690 |
| 2009/0057567 A1* | 3/2009 | Bykanov | G03F 7/70033 |
| | | | 250/429 |
| 2013/0058783 A1* | 3/2013 | Fukuda | F04D 25/0613 |
| | | | 415/227 |
| 2016/0209753 A1* | 7/2016 | Zhao | G03F 7/70033 |

FOREIGN PATENT DOCUMENTS

| | | |
|---|---|---|
| JP | H 3-30448 A | 2/1991 |
| WO | WO 2005/031169 A1 | 4/2005 |
| WO | WO 2015/055374 A1 | 4/2015 |

OTHER PUBLICATIONS

International Preliminary Report on Patentability and Written Opinion of the International Searching Authority directed to related International Patent Application No. PCT/EP2015/068466, dated Mar. 14, 2017; 8 pages.

* cited by examiner

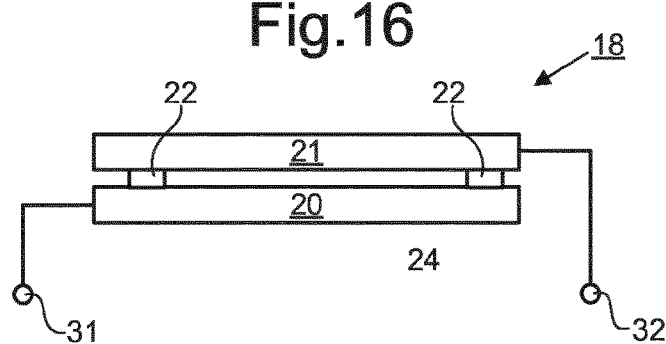
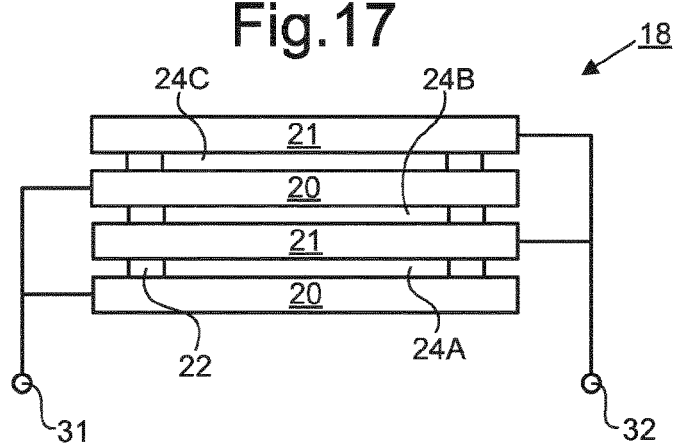
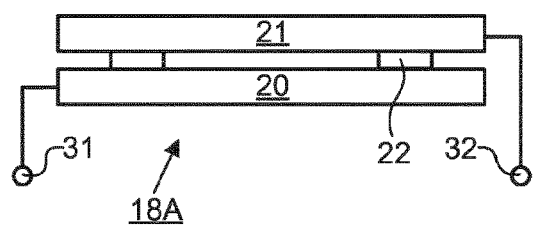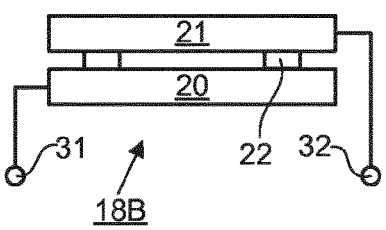
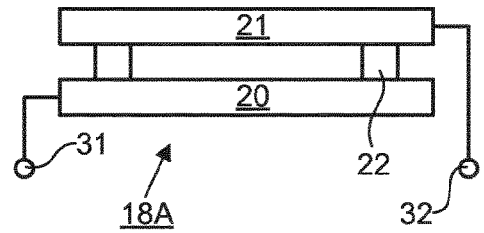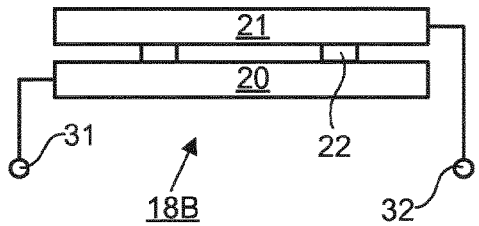

DEVICE FOR MONITORING A RADIATION SOURCE, RADIATION SOURCE, METHOD OF MONITORING A RADIATION SOURCE, DEVICE MANUFACTURING METHOD

CROSS-REFERENCE TO RELATED APPLICATIONS

This application claims the benefit of EP application 14184445.6, which was filed on 11 Sep. 2014, and which is incorporated herein in its entirety by reference.

FIELD

An embodiment of the invention relates to a device for monitoring a radiation source for a lithography apparatus, a radiation source, a method of monitoring a radiation source, and a device manufacturing method. This embodiment relates particularly to measuring a concentration of a vapor or of an amount of a deposit from the vapor in the radiation source using one or more capacitors. Control of the radiation source may be implemented based the measured concentration of vapor or amount of deposit.

BACKGROUND

Lithography is widely recognized as one of the key steps in the manufacture of integrated circuits (ICs) and other devices and/or structures. However, as the dimensions of features made using lithography become smaller, lithography is becoming a more critical factor for enabling miniature IC or other devices and/or structures to be manufactured.

A lithography apparatus is a machine that applies a desired pattern onto a substrate, usually onto a target portion of the substrate. A lithography apparatus can be used, for example, in the manufacture of ICs. In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned.

In order to shorten the exposure wavelength and, thus, reduce the minimum printable size, it has been proposed to use an extreme ultraviolet (EUV) radiation source. EUV radiation sources are typically configured to output radiation wavelengths of around 5-20 nm, for example, 13.5 nm or about 13 nm or 6.5-6.8 nm. Use of EUV radiation may constitute a significant step toward achieving small features printing. Such radiation is termed extreme ultraviolet or soft x-ray, and possible sources include, for example, laser-produced plasma sources, discharge plasma sources, or synchrotron radiation from electron storage rings.

SUMMARY

In radiation sources that generate a plasma, such as a laser produced plasma source and a discharge plasma source, a fuel may be vaporized to produce the plasma. The fuel may comprise Sn, Li, Gd or Tb for example. A vapor of the fuel may be referred to as a fuel vapor. A gas flow may be provided for removing fuel vapor from the radiation source. The fuel or fuel vapor may react with the gas in the gas flow to produce a fuel reaction product vapor. In the case where the fuel comprises Sn, the reaction product may comprise stannane.

Fuel vapor or fuel reaction product vapor can condense onto surfaces in the radiation source forming deposits of the fuel or fuel reaction product. These deposits can reduce the performance of the radiation source in various ways. For example, the deposits may form in gas delivery channels for providing a gas flow for removing the fuel vapor. The deposits may reduce the cross-sectional area in the gas delivery channels, thereby impeding the gas flow. The deposits may form in a channel structure of a contaminant trap configured to prevent contaminants passing from a source chamber in which the plasma is created to regions downstream of the source chamber. The deposits may block EUV radiation and thereby reduce an output power of the radiation source.

It is difficult to predict where and at what rate the deposits will build up. Collecting information about the deposits can only currently be performed when the radiation source is offline. Collecting such information therefore reduces the availability of the radiation source. The radiation source may be brought offline for cleaning more frequently than is necessary because of the inability to obtain detailed information about the deposits while the radiation source is online. Bringing the radiation source offline more frequently than is necessary also reduces the availability of the radiation source.

Creation of radiation from plasma in a radiation source is a complex process. Various operating parameters of the radiation source need to be controlled to achieve high and stable output power. Variations of the output power can be monitored and used as input to controllers that control operating parameters of the radiation source. However, the monitored variations of output power provide only limited information. The response of the controllers to the monitored variations is not therefore optimal.

It is an object of the invention to at least partially address one or more of the problems with the prior art discussed above.

According to an aspect of the invention, there is provided a device for monitoring a radiation source for a lithography apparatus, the radiation source being configured to produce radiation by generating a plasma from a fuel, the device comprising: one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor; and a measurement system configured to output, for at least one of the one or more capacitors, one or both of a measure of a concentration of the vapor in the gap of the capacitor and a measure of an amount of the deposit in the gap of the capacitor, by measuring a capacitance, or a parameter dependent on the capacitance, of at least one of the one or more capacitors.

According to an aspect of the invention, there is provided a method of monitoring a radiation source for a lithography apparatus, the radiation source being configured to produce radiation by generating a plasma from a fuel, the method comprising: providing one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor; and measuring a capacitance, or a parameter dependent on the capacitance, of at least one of the one or more capacitors and using the measured capacitance or parameter to provide an output comprising one or both of a measure of a concentration of the vapor in the gap of the capacitor and a measure of an amount of the deposit in the gap of the capacitor.

According to an aspect of the invention, there is provided a device manufacturing method, comprising: using a radiation source to supply radiation to a lithography apparatus; using the lithography apparatus to manufacture a device; and controlling the radiation source by: providing one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor; measuring a capacitance, or a parameter dependent on the capacitance, of at least one of the one or more capacitors and using the measured capacitance or parameter to provide an output comprising one or both of a measure of a concentration of the vapor in the gap of the capacitor and a measure of an amount of the deposit in the gap of the capacitor; and using a controller to control one or more operating parameters of the radiation source using the output.

Further aspects, features, and potential advantages, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention are described below, by way of example only, with reference to the accompanying drawings, in which:

FIG. 16 depicts schematically how electrical connections may be made to a capacitor comprising two parallel plates;

FIG. 17 depicts schematically how electrical connections may be made to a capacitor comprising more than two plates;

FIGS. 18 and 19 depict schematically a pair of first and second capacitors in which the first capacitor, shown in FIG. 18, has conductors with larger surfaces areas than the second capacitor, shown in FIG. 19;

FIGS. 20 and 21 depict schematically an alternative pair of first and second capacitors in which the first capacitor, shown in FIG. 20, has conductors that are separated by a larger distance than the second capacitor, shown in FIG. 21;

DETAILED DESCRIPTION

Figure 1:
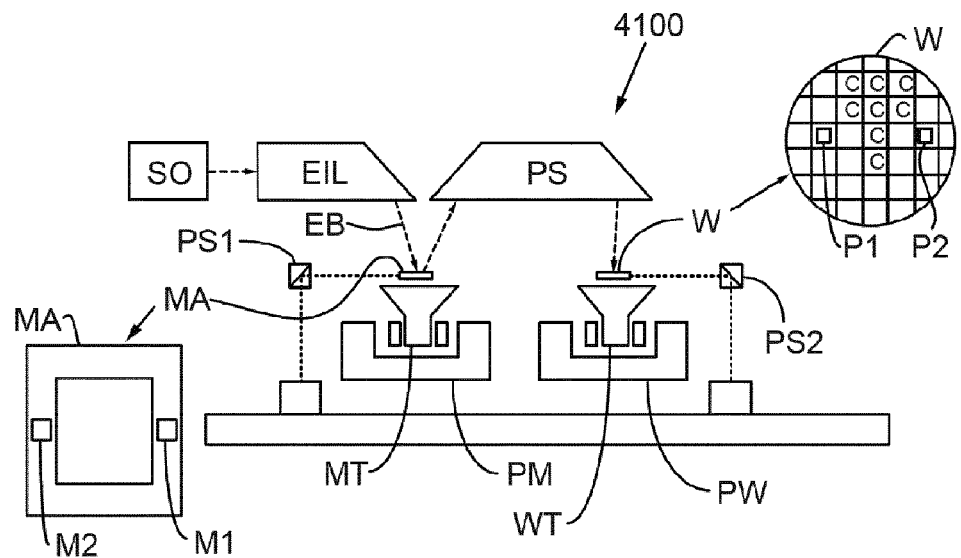
FIG. 1 depicts schematically a lithography apparatus having reflective optics according to embodiments of the invention.

FIG. 1 schematically depicts a lithography apparatus 4100, including a source collector module SO, according to an embodiment of the invention. The apparatus comprises: an illumination system (illuminator) EIL configured to condition a exposure beam EB (e.g. EUV radiation); a support structure (e.g. a mask table) MT constructed to support a patterning device (e.g. a mask or a reticle) MA and connected to a first positioner PM configured to accurately position the patterning device; a substrate table (e.g. a wafer table) WT constructed to hold a substrate (e.g. a resist-coated wafer) W and connected to a second positioner PW configured to accurately position the substrate; and a projection system (e.g. a reflective projection system) PS configured to project a pattern imparted to the exposure beam EB by patterning device MA onto a target portion C (e.g. comprising one or more dies) of the substrate W.

The support structure MT holds the patterning device MA in a manner that depends on the orientation of the patterning device, the design of the lithography apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system.

The term "patterning device" should be broadly interpreted as referring to any device that can be used to impart a radiation beam with a pattern in its cross-section such as to create a pattern in a target portion of the substrate. The pattern imparted to the radiation beam may correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The projection system, like the illumination system, may include various types of optical components, such as refractive, reflective, magnetic, electromagnetic, electrostatic or other types of optical components, or any combination thereof, as appropriate for the exposure radiation being used, or for other factors such as the use of a vacuum. It may be desirable to use a vacuum for EUV radiation since gases may absorb too much radiation. A vacuum environment may therefore be provided to the whole beam path with the aid of a vacuum wall and vacuum pumps.

As here depicted, the apparatus is of a reflective type (e.g. employing a reflective mask).

The lithography apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

Referring to FIG. 1, the illuminator EIL receives an extreme ultra violet radiation beam from the source collector module SO. Methods to produce EUV radiation include, but are not necessarily limited to, converting a material into a plasma state that has at least one element, e.g., xenon, lithium or tin, with one or more emission lines in the EUV range. In one such method, often termed laser produced plasma ("LPP") the desired plasma can be produced by irradiating a fuel, such as a droplet, stream or cluster of material having the required line-emitting element, with a laser beam. The source collector module SO may be part of an EUV radiation system including a laser, not shown in FIG. 1, for providing the laser beam exciting the fuel. The resulting plasma emits output radiation, e.g. EUV radiation, which is collected using a radiation collector, disposed in the source collector module. The laser and the source collector module may be separate entities, for example when a $CO_2$ laser is used to provide the laser beam for fuel excitation.

In such cases, the laser is not considered to form part of the lithography apparatus and the radiation beam is passed from the laser to the source collector module with the aid of a beam delivery system comprising, for example, suitable directing mirrors and/or a beam expander. In other cases the source may be an integral part of the source collector module, for example when the source is a discharge produced plasma EUV generator, often termed as a DPP source.

The illuminator EIL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator EIL may comprise various other components, such as faceted field and pupil mirror devices. The illuminator EIL may be used to condition the radiation beam, to have a desired uniformity and intensity distribution in its cross-section.

The exposure beam EB is incident on the patterning device (e.g., mask) MA, which is held on the support structure (e.g., mask table) MT, and is patterned by the patterning device MA. After being reflected from the patterning device (e.g. mask) MA, the exposure beam EB passes through the projection system PS, which focuses the beam onto a target portion C of the substrate W. With the aid of the second positioner PW and position sensor PS2 (e.g. an interferometric device, linear encoder or capacitive sensor), the substrate table WT can be moved accurately, e.g. so as to position different target portions C in the path of the exposure beam EB. Similarly, the first positioner PM and another position sensor PS1 can be used to accurately position the patterning device (e.g. mask) MA with respect to the path of the exposure beam EB. Patterning device (e.g. mask) MA and substrate W may be aligned using mask alignment marks M1, M2 and substrate alignment marks P1, P2.

The lithography apparatus can operate in a scan mode in which the support structure (e.g. mask table) MT and the substrate table WT are scanned synchronously while a pattern imparted to the exposure beam EB is projected onto a target portion C (i.e. a single dynamic exposure). The velocity and direction of the substrate table WT relative to the support structure (e.g. mask table) MT may be determined by the (de-)magnification and image reversal characteristics of the projection system PS.

Figure 2:
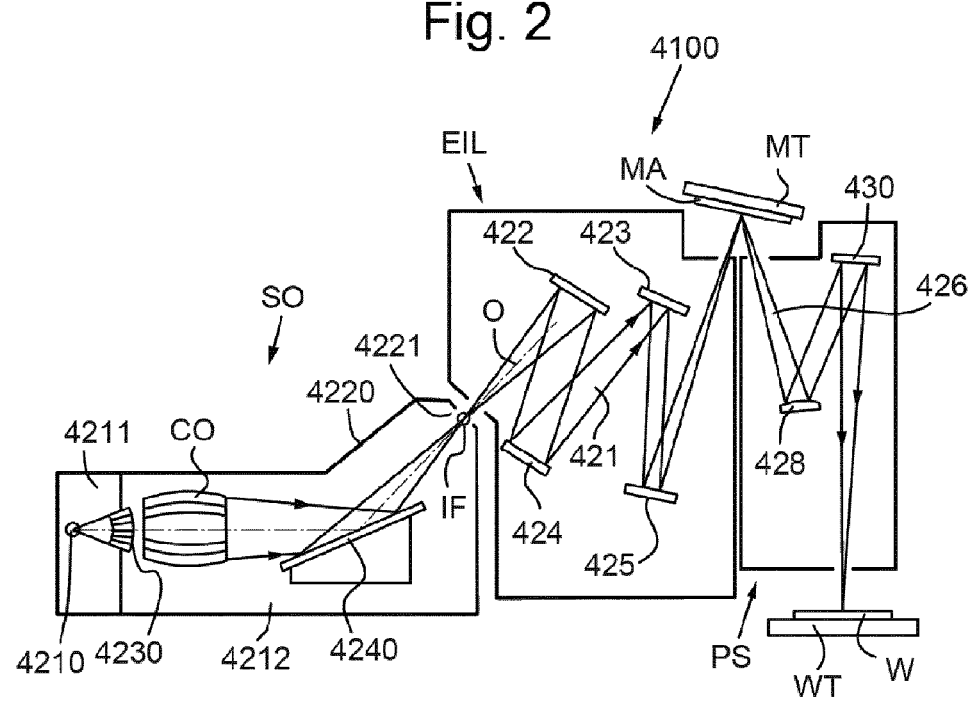
FIG. 2 is a more detailed view of the apparatus of FIG. 1.

FIG. 2 shows the lithography apparatus 4100 in more detail, including the source collector module SO, the illuminator EIL, and the projection system PS. The source collector module SO is constructed and arranged such that a vacuum environment can be maintained in an enclosing structure 4220 of the source collector module SO. A plasma 4210 which emits EUV radiation may be formed by a laser produced plasma source. EUV radiation may be produced by a gas or vapor, for example Xe gas, Li vapor or Sn vapor in which the plasma 4210 is created to emit radiation in the EUV range of the electromagnetic spectrum. The plasma 4210 is created by, for example, a pulsed laser beam. Partial pressures of, for example, 10 Pa of Xe, Li, Sn, Gd or Tb vapor or any other suitable gas or vapor may be needed for efficient generation of the radiation. In an embodiment, a plasma of excited tin (Sn) is provided to produce EUV radiation.

The radiation emitted by the plasma 4210 is passed from a source chamber 4211 into a collector chamber 4212 via an optional gas barrier or contaminant trap 4230 (in some cases also referred to as contaminant barrier or foil trap), which is positioned in or behind an opening in source chamber 4211. The contaminant trap 4230 may include a channel structure. Contamination trap 4230 may also include a gas barrier or a combination of a gas barrier and a channel structure.

The collector chamber 4212 may include a radiation collector CO which may be a so-called grazing incidence collector. Radiation that traverses collector CO can be reflected off a grating spectral purity filter 4240 to be focused in a virtual source point IF. The virtual source point IF is commonly referred to as the intermediate focus, and the source collector module is arranged such that the intermediate focus IF is located at or near an opening 4221 in the enclosing structure 4220. The virtual source point IF is an image of the radiation emitting plasma 4210.

Subsequently the radiation traverses the illuminator EIL, which may include a faceted field mirror device 422 and a faceted pupil mirror device 424 arranged to provide a desired angular distribution of the exposure beam EB, at the patterning device MA, as well as a desired uniformity of radiation intensity at the patterning device MA. The faceted field mirror device 422 has a plurality of filed facets. The faceted pupil mirror device has a plurality of pupil facets. The illuminator EIL also includes illuminator mirrors 423, 425 which cooperate with faceted pupil mirror device 424 to project an image of each facet of faceted field mirror device 422 onto an illumination field (also referred to as the slit) IS. The illuminator EIL is arranged to provide Köhler illumination of the illumination slit IS.

Upon reflection of the exposure beam EB at the patterning device MA, held by the support structure MT, a patterned beam 426 is formed and the patterned beam 426 is imaged by the projection system PS via reflective elements 428, 430 onto a substrate W held by the wafer stage or substrate table WT.

More elements than shown may generally be present in illuminator EIL and projection system PS. The grating spectral purity filter 4240 may optionally be present, depending upon the type of lithography apparatus. Further, there may be more mirrors present than those shown in the Figures, for example there may be 1-6 additional reflective elements present in the projection system PS than shown in FIG. 2.

Collector CO, as illustrated in FIG. 2, is depicted as a nested collector with grazing incidence reflectors, just as an example of a collector (or collector mirror). A collector CO of this type is desirably used in combination with a discharge produced plasma source, often called a DPP source.

In an embodiment, the source collector module SO may be part of an LPP radiation system. A laser arranged to deposit laser energy into a fuel, such as xenon (Xe), tin (Sn), lithium (Li), gadolinium (Gd) or Terbium (Tb) is used to create a highly ionized plasma 4210 with electron temperatures of several tens of eV. The energetic radiation generated during de-excitation and recombination of these ions is emitted from the plasma, collected by a near normal incidence collector CO and focused onto the opening 4221 in the enclosing structure 4220.

As mentioned in the introductory part of the description, vapor generated by creating plasmas from fuel (e.g. by depositing laser energy into the fuel in an LPP radiation system) can condense on structures within the radiation source. There is a lack in the prior art of methods for monitoring concentrations of vapor while the radiation source is online. There is also a lack in the prior art of methods for monitoring amounts (e.g. thicknesses) of deposits formed from the vapor while the radiation source is online. It has therefore been difficult to predict where deposits formed from the vapor occur. It has been difficult to predict the speed of formation of the deposits. In the following embodiments, methods and apparatus are described that allow online monitoring of vapor concentrations and/or of amounts of deposits formed from the vapor at different locations in the radiation source. This online monitoring makes it possible to understand in real time how deposits form within the radiation source. It is no longer necessary to perform offline inspections to determine whether deposits have formed to a level which means that cleaning of the radiation source is required. The radiation source can therefore be kept online for longer Keeping the radiation source online for longer can improve productivity. The speed of formation of the deposits can be determined easily in a plurality of different locations within the radiation source. Determining how the speed of formation of the deposits varies with position may provide valuable information that allows the radiation source to be modified to reduce the damaging effects of deposits. In an embodiment, concentrations of vapor can be monitored online at different locations. Monitoring how concentrations of vapor vary with position may provide valuable information about flow patterns of the vapor within the radiation source. Understanding flow patterns within the radiation source may allow modification of the radiation source to improve performance or reduce the speed of formation of deposits on selected structures (e.g. structures which are more seriously affected by deposits than other structures) within the radiation source.

The methods and apparatus used for the online monitoring can also provide valuable information on how the radiation source is operating. According to embodiments, the information on how the radiation source is operating may be used to improve control of one or more operating parameters of the radiation source. Improving control of one or more operating parameters of the radiation source may improve the performance of the radiation source. For example, the stability or output power of the radiation source may be improved.

Figure 3:
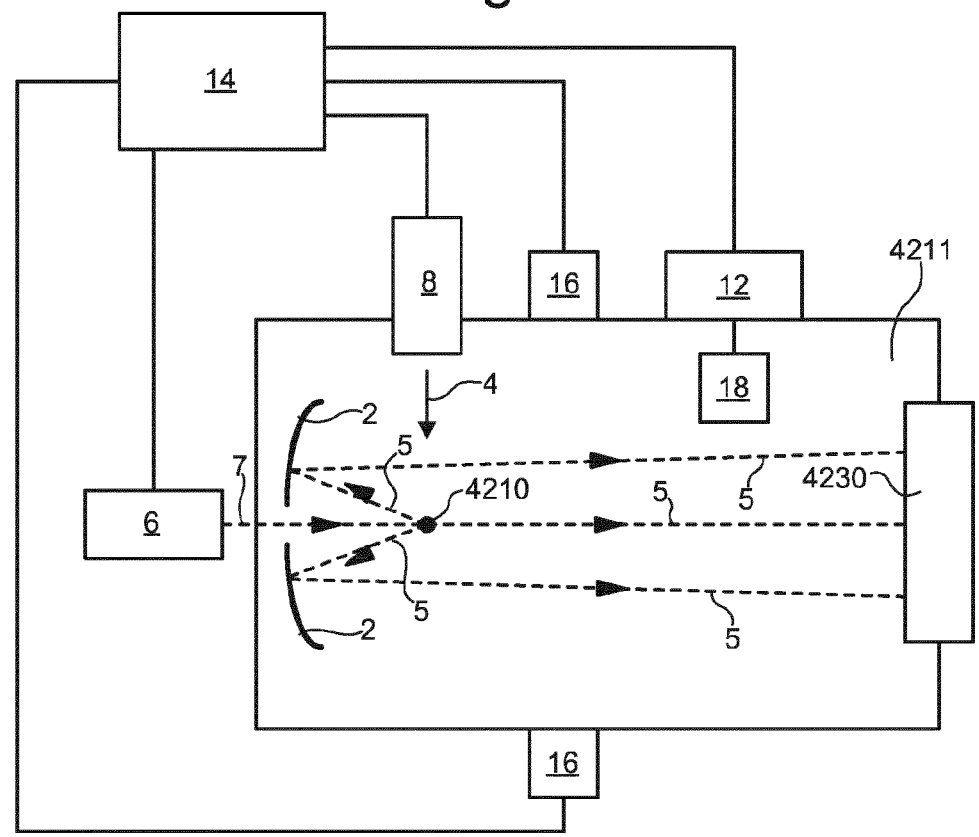
FIG. 3 depicts schematically a device for controlling a radiation source according to an embodiment.

An example of a device for monitoring a radiation source for a lithography apparatus according to an embodiment is depicted in FIG. 3. The device comprises one or more capacitors 18. FIGS. 4-24 depict various example configurations for the one or more capacitors 18. Each of the capacitors 18 comprises at least two conductors 20 and 21. The two conductors 20 and 21 are mounted such that a vapor in the radiation source can flow through a gap 24 between the conductors 20 and 21. The concentration of the vapor in the gap 24 has an effect on the capacitance of the capacitor 18 by changing the permittivity in the gap 24. The amount of a deposit formed from the vapor (e.g. by condensation) in the gap 24 also has an effect on the capacitance of the capacitor 18. The change in capacitance due to the deposits may be considered to be the result of a change in the permittivity in the gap 24. Alternatively, when the deposits are metallic, the change in capacitance may be considered to be the result of a change in the separation between the conductors 20,21. When the deposits are metallic the deposits are electrically conducting and effectively form part of the conductors 20,21.

The device further comprises a measurement system 12. The measurement system 12 is configured to output, for at least one of the one or more capacitors 18, one or both of a measure of a concentration of the vapor in the gap 24 of the capacitor 18 and a measure of an amount of the deposit in the gap 24 of the capacitor 18. Thus, a measure of the concentration of the vapor in the gap may be output, a measure of an amount of the deposit in the gap may be output, or both a measure of the concentration of the vapor in the gap and a measure of the amount of the deposit in the gap may be output. The measure of the concentration or the measure of the amount of the deposit is obtained by measuring a capacitance, or a parameter dependent on the capacitance, of at least one of the one or more capacitors 18.

As will be described in further detail below, where both the vapor and the deposit are present it may be necessary to measure the capacitance (or a parameter dependent on the capacitance) of at least two different capacitors in order to distinguish between the effects on the capacitance caused by the vapor and the effects on the capacitance caused by the deposit (and thereby allow output of independent measures of the concentration of the vapor and the amount of the deposit).

The skilled person would be aware of a variety of methods for measuring a capacitance or a parameter that is dependent on the capacitance. For example, the capacitance of a capacitor 18 may be measured directly by applying a known current (or voltage) to the capacitor 18 and measuring the resulting voltage (or current). Alternatively the capacitor 18 may be incorporated into a resonant circuit. The resonant frequency of the resonant circuit may depend on the capacitance of the capacitor 18. The resonant frequency is therefore an example of a parameter that is dependent on the capacitance of the capacitor 18. Measuring the resonant frequency provides a measure of a parameter that is dependent on the capacitance of the capacitor 18. Measuring the resonant frequency may also be considered to be a measurement of the capacitance itself if the relationship between the resonant frequency and the capacitance is known. The resonant circuit may be an RC-circuit for example. Alternatively or additionally, one or more other properties of the resonant circuit or RC-circuit that are dependent on the capacitance of the capacitor may be measured. Such properties of the resonant circuit may comprise gain or sensitivity. Alternatively or additionally, a circuit containing the capacitor 18 (e.g. a resonant circuit or an RC-circuit) may be tuned to a resonant point. The amount of tuning that is required may provide information about the capacitance of the capacitor 18 and thereby provide a measure of the capacitance. The amount of tuning required may also be considered to be a parameter that is dependent on the capacitance of the capacitor 18.

Reference is made herein to outputting a measure of a concentration of the vapor. The measure of the concentration may comprise the concentration itself or a parameter that is dependent on the concentration (and which is therefore indicative of the concentration). Reference is made herein to outputting a measure of an amount of a deposit. The measure of the amount of the deposit may comprise the amount itself or a parameter that is dependent on the amount (and which is therefore indicative of the amount).

In an embodiment, the radiation source is configured to vaporize a fuel using a laser (e.g. a laser produced plasma source or discharge produced plasma source). FIG. 3 depicts an example configuration. Arrow 7 illustrates schematically how an output from a laser delivery system 6 is directed into a source chamber 4211. The laser delivery system 6 may comprise a laser and a beam delivery system. The output from the laser delivery system 6 deposits laser energy into a flow of fuel (arrows 4) provided by a fuel delivery system 8. Depositing laser energy into the fuel may vaporize the fuel and lead to the generation of a plasma 4210. Arrows 5 illustrate schematically how EUV radiation generated by the plasma 4210 propagates out of the source chamber 4211 (either directly or after reflection from mirrors 2). In the particular embodiment shown, the EUV radiation is directed through a contaminant trap 4230. A collector chamber 4212 (not shown in FIG. 3 but described above with reference to FIG. 2) may be provided downstream from the contaminant trap 4230.

The efficiency of the radiation source may depend on how efficiently the laser delivery system 6 converts fuel into plasma. The efficiency of the conversion may depend on how accurately the output 7 from the laser delivery system 6 strikes the fuel. For example, the flow of fuel may comprise a flow of droplets of fuel. The output 7 may comprise a sequence of pulses of laser radiation. In such an embodiment, the efficiency of the conversion may depend on how accurately the pulses of laser radiation strike the droplets of fuel.

Each droplet of fuel may be hit by one pulse of radiation. Alternatively, each droplet of fuel may be hit by multiple pulses of radiation. For example, each droplet may be hit by a first pulse (which may be referred to as a pre-pulse) and a second pulse (which may be referred to as a main pulse). The pre-pulse may be configured to change the shape of the droplet. The change in shape of the droplet may comprise flattening of the droplet for example. The main pulse may be configured to vaporize the droplet after the shape of the droplet has been changed by the pre-pulse.

Various factors can affect how accurately the output 7 from the laser delivery system 6 strikes the fuel. These factors may include one or more of the following: the timing of the pulses of the laser, the trajectory of the pulses of the laser, the shapes of the pulses of the laser, the sizes of the pulses of the laser, the position of focus of the pulses of the laser, the timing of the droplets of the fuel, the trajectory of the droplets of the fuel, the shapes of the droplets of the fuel, and the sizes of the droplets of fuel.

The efficiency of the conversion of fuel into plasma may also depend on other factors. For example, the energies of the pulses of the laser may affect the efficiency. The energy of the laser pulses may be particularly important where the sequence of pulses comprises pre-pulses and main pulses. The shape of the droplet after being hit by the pre-pulse may depend sensitively on the energy of the pre-pulse.

In an embodiment, the device for monitoring a radiation source further comprises a controller 14. The controller 14 may be configured to use the measure of the concentration of the vapor obtained by the measurement system 12 to control one or more operating parameters of the radiation source. Alternatively or additionally, the controller 14 may be configured to use the measure of the amount of the deposit obtained by the measurement system 12 to control one or more operating parameters of the radiation source.

In an embodiment, the one or more operating parameters comprise one or more operating parameters of the laser delivery system 6. The one or more operating parameters of the laser delivery system 6 may control one or more of the following factors: the timing of the pulses of the laser, the trajectory of the pulses of the laser, the shapes of the pulses of the laser, the sizes of the pulses of the laser, the position of focus of the pulses of the laser, and the energies of the pulses of the laser.

In an embodiment, alternatively or additionally, the one or more operating parameters comprise one or more operating parameters of the fuel delivery system 8. The one or more operating parameters of the fuel delivery system 8 may control one or more of the following factors: the timing of the droplets of the fuel, the trajectory of the droplets of the fuel, the shapes of the droplets of the fuel, and the sizes of the droplets of fuel.

In an embodiment the radiation source further comprises a gas delivery system 16 configured to provide a flow of gas through the radiation source. The flow of gas through the radiation source carries away vapor (e.g. fuel or fuel reaction products) and thereby controls the level of vapor in the radiation source. The gas delivery system 16 may be controlled by the controller 14. The one or more operating parameters of the radiation source controlled by the controller 14 using the concentration measured by the measurement system 12 may include one or more operating parameters of the gas delivery system. The one or more operating parameters of the gas delivery system 16 may control a rate of flow of gas through the radiation system for example.

In an embodiment the controller 14 is configured to respond to the measure of the concentration of vapor obtained by the measurement system 12 falling below a lower threshold value by controlling the one or more operating parameters of the radiation source to increase the concentration of the vapor. The one or more operating parameters of the radiation source may be controlled so as to increase a rate of generation of the plasma. For example, the fall in the concentration of vapor may occur because of a fall in the efficiency of the process of depositing laser energy into the fuel. In this case, the controller 14 may control one or more operating parameters of either or both of the laser delivery system 6 and the fuel delivery system 8 to try and increase the efficiency of the depositing of laser energy into the fuel. Increasing the efficiency of the depositing of laser energy into the fuel may increase the rate of generation of the plasma.

In an embodiment the controller 14 is configured to respond to the concentration of vapor measured by the measurement system 12 rising above a predetermined value by controlling one or more operating parameters of the gas delivery system 16. For example, the rate of flow of gas delivered by the gas delivery system may be increased so as to carry vapor away more quickly and thereby reduce the concentration of vapor.

In an embodiment, the controller 14 is configured to detect when the measure of the amount of the deposit measured by the measurement system 12 rises above an upper threshold value. In an embodiment, the controller 14 is further configured to output an alarm signal indicating that the measure of the amount of the deposit measured by the measurement system 12 has risen above the upper threshold value. Alternatively or additionally, the controller 14 may be configured to initiate a cleaning procedure. Alternatively or additionally, the controller 14 may be configured to cause the radiation source to enter a safety mode or to shut down.

In the embodiment shown in FIG. 3, the output from the measurement system 12 is used as input to the controller 14 in order to allow control of the one or more operating parameters of the radiation source. However, it is not essential that the output from the measurement system 12 be used to control the one or more operating parameters of the radiation source. In other embodiments the output from the measurement system 12 may be used for research or diagnostic purposes. The output from the measurement system 12 may be used to detect when the radiation source needs to be taken offline for cleaning for example. The output from the measurement system 12 may be used to help with redesign of the radiation source to reduce problems of deposits from the vapor.

Figure 4:
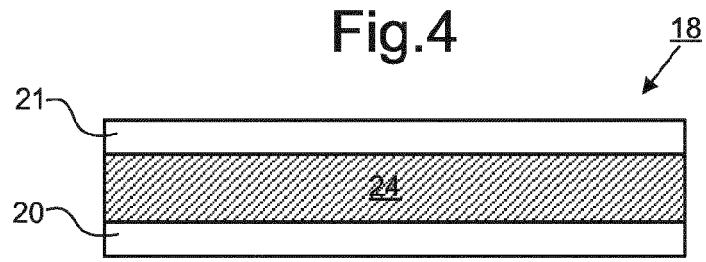
FIG. 4 is a schematic side view of a capacitor showing a gap between conductors.
Figure 5:
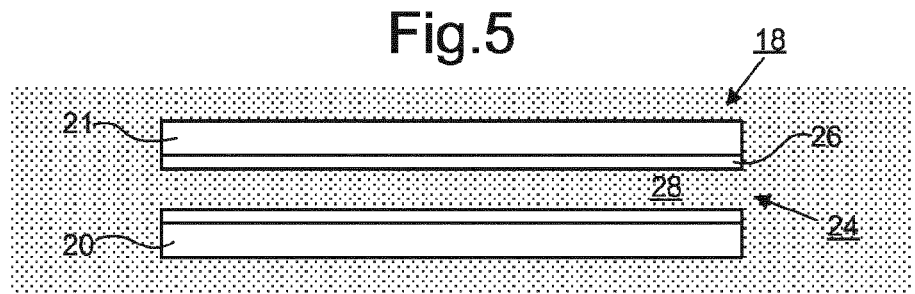
FIG. 5 is a schematic side view of the capacitor of FIG. 4 with a concentration of vapor and a layer of deposit formed from the vapor in the gap between the conductors.

FIG. 4 is a side view illustrating an example capacitor 18. The capacitor 18 in this example comprises two square, parallel conductors 20,21. The shape of the conductors 20,21 is not limited to square. Any other shape may be used. The conductors 20,21 may be substantially planar. The conductors 20,21 may be referred to as plates. The capacitor 18 shown may be referred to as a parallel plate capacitor. In other embodiments, the conductors 20,21 are not planar. The conductors 20,21 may be curved or elongate (e.g. in the form of individual wires or a network of wires). The conductors 20,21 may be curved in 2D dimensions (e.g. so that the conductors are straight when viewed in one direction and curved when viewed perpendicularly to the one direction, for example where the conductors 20,21 comprise portions of a cylinder) or curved in 3D dimensions (e.g. where the conductors 20,21 comprise portions of a sphere). A gap 24 is provided between the conductors 20,21. The conductors 20,21 are mounted so that the gap allows vapor to flow through the gap 24. The gap 24 is not therefore filled with a solid dielectric (insulating) material. FIG. 5 illustrates the same capacitor 18 in use in a radiation source. The capacitor 18 is exposed to a vapor 28 which can flow through the gap 24. Layer 26 of deposit of the vapor have built up in the gap 24. In this example the layers 26 are conducting. For the purposes of calculating the capacitance the layers 26 may be considered as forming part of the conductors 20,21. The layers 26 therefore effectively causes the separation between the conductors to be reduced.

The capacitance, C, of a parallel plate capacitor is given by the following expression:

$$C = \varepsilon A/d$$

where $\varepsilon = \varepsilon_0 \varepsilon_r$ with $\varepsilon_0$ being the permittivity of free space and $\varepsilon_r$ being the relative permittivity of the material in the gap between the conductors of the capacitor. A is the surface area of one face of each conductor. d is the separation between the conductors.

Figure 6:
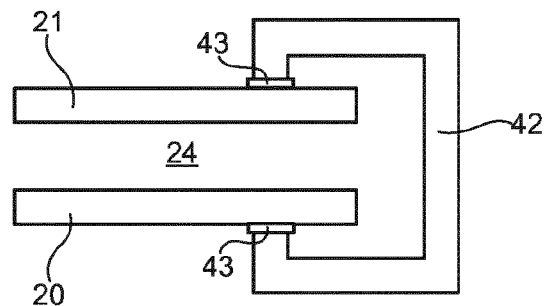
FIG. 6 depicts schematically a conductor holding structure configured to hold conductors of a capacitor via connections that are outside of a gap between the conductors.

In an embodiment the conductors 20,21 are mounted so as to be completely separated from each other. An example of such an embodiment is shown in FIG. 6. In this case, with the exception of any deposit from the vapor, all of the region in between the conductors 20,21 is filled only with gaseous material. In such an embodiment (and in other embodiments), a conductor holding structure 42 may be provided for holding the conductors 20,21 in position. The conductor holding structure 42 may be configured to hold the conductors 20,21 via connections 43 that are outside of the gap 24 between the conductors 20,21.

Figure 7:
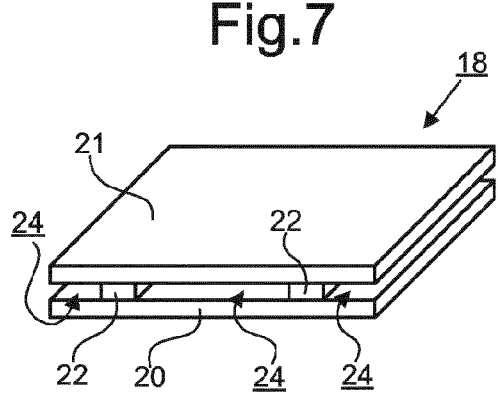
FIG. 7 is a schematic perspective view of a capacitor for use in an embodiment.
Figure 8:
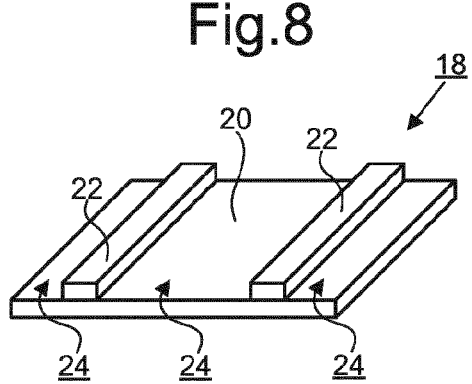
FIG. 8 is a schematic perspective view of the capacitor of FIG. 7 with an uppermost conductor removed to reveal an example configuration of dielectric spacers.
Figure 9:
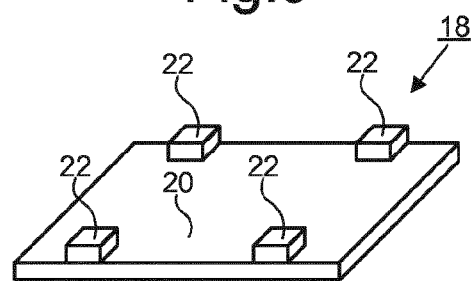
FIG. 9 is a schematic perspective view of an alternative capacitor with an uppermost conductor removed to reveal an alternative example configuration of dielectric spacers.
Figure 10:
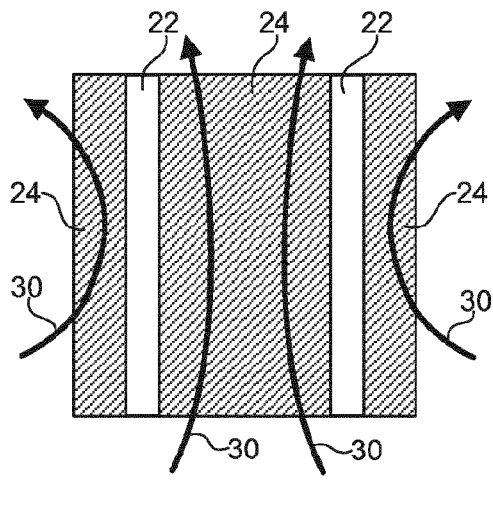
FIG. 10 is a schematic top view of the capacitor of FIG. 7 with uppermost conductor removed showing example flow paths for vapor in gaps of the capacitor.
Figure 11:
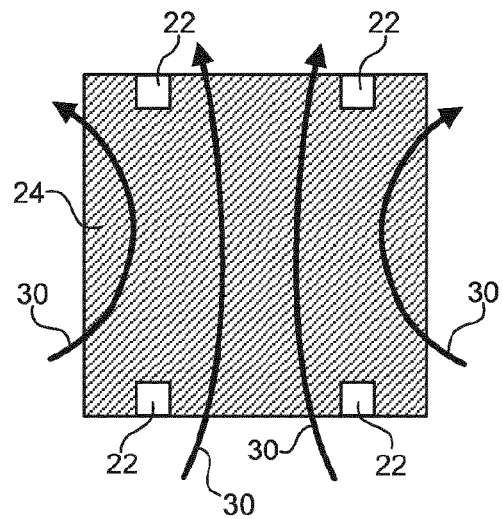
FIG. 11 is a schematic top view of the capacitor of FIG. 9 with uppermost conductor removed showing example flow paths for vapor in a gap of the capacitor.

In other embodiments the conductors 20,21 may be connected to each other by one or more dielectric spacer elements 22. The use of dielectric spacer elements 22 may facilitate manufacture and/or sturdiness of the capacitor 18. Examples of embodiments having dielectric spacer elements 22 are shown in FIGS. 7-11. In other embodiments, spacer elements that are insulating but not necessarily dielectric may be used in an equivalent manner. Such spacer elements may be referred to as isolators. FIG. 7 is a perspective view of a capacitor 18 having two linear dielectric spacer elements 22. FIG. 8 shows the capacitor of FIG. 7 with the uppermost conductor 21 removed to show the dielectric spacer elements 22. FIG. 9 shows an alternative arrangement of dielectric spacer elements 22. FIGS. 10 and 11 are top views looking down onto the examples of FIGS. 8 and 9. Arrows 30 show example flow patterns for vapor flowing through the gap 24 between the conductors 20,21. The arrows 30 show that the vapor can flow freely through the gap 24 rather than, for example, merely being absorbed in pores present in the gap. If the gap 24 were filled with a porous material the vapor would not be able to flow through the gap 24. Filling the gap 24 with porous material is therefore less desirable. In embodiments of the invention the gap 24 is completely devoid of any porous material. In embodiments of the invention one or more of the capacitors 18 is devoid of any porous material. If the vapor can enter the gap 24 but not flow through the gap 24, deposits formed from the vapor will tend to block flow paths for the vapor in the gap 24. Blocking of flow paths will restrict entry of vapor and reduce how accurately the concentration of the vapor can be measured.

Each of one or more of the capacitors 18 may comprise two or more conductors 20,21 that belong only to that capacitor 18. Alternatively or additionally, each of one or more of the capacitors 18 may comprise one or more conductors 20 that are shared between two or more of the capacitors 18. FIGS. 12-15 depict example configurations in which a plurality of capacitors 18 share a conductor 20.

Figure 12:
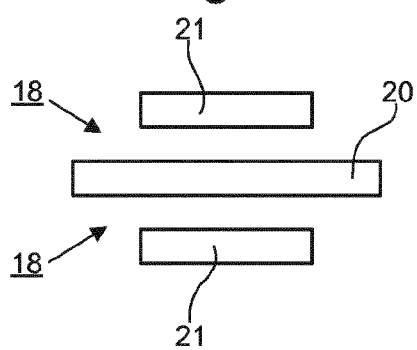
FIG. 12 depicts schematically an example plurality of capacitors comprising a shared conductor that is planar in section.

In the example of FIG. 12, the shared conductor 20 has a planar form. The shared conductor 20 is shared between two capacitors 18. A first of the two capacitors 18 is formed from the combination of the uppermost conductor 21 and the shared conductor 20. A second of the two capacitors 18 is formed from the combination of the lowermost conductor 21 and the shared conductor 20.

Figure 13:
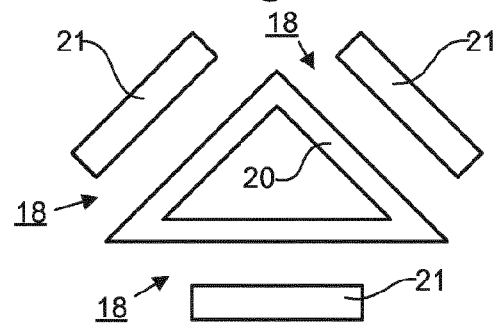
FIG. 13 depicts schematically an example plurality of capacitors comprising a shared conductor that is triangular in section.

In the example of FIG. 13, the shared conductor 20 has a triangular form in section. The shared conductor 20 is shared between three capacitors 18. Each of the three capacitors 18 is formed from the combination of one of the three outer conductors 21 and the shared conductor 20.

Figure 14:
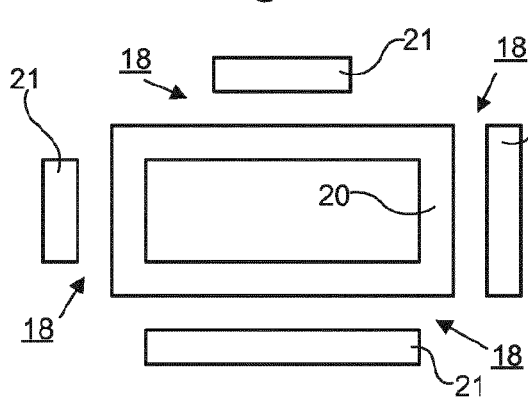
FIG. 14 depicts schematically an example plurality of capacitors comprising a shared conductor that is rectangular in section.

In the example of FIG. 14, the shared conductor 20 has a rectangular form in section. The shared conductor 20 is shared between four capacitors 18. Each of the four capacitors 18 is formed from the combination of one of the outer conductors 21 and the shared conductor 20.

Figure 15:
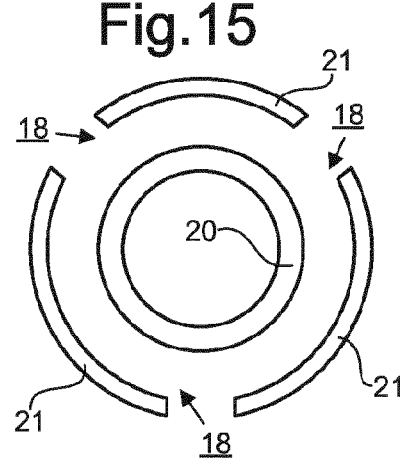
FIG. 15 depicts schematically an example plurality of capacitors comprising a shared conductor that is circular in section.

In the example of FIG. 15, the shared conductor 20 has a circular form in section. The shared conductor 20 is shared between three capacitors 18. Each of the three capacitors 18 is formed from the combination of one of the outer conductors 21 and the shared conductor 20.

In embodiments using shared conductors 20 of the type shown in FIGS. 12-15, and in embodiments using shared conductors 20 of other forms, the conductors 21 that are not shared may all have the same surface areas (as in the examples of FIGS. 12, 13 and 15) or may have two or more different surface areas (as in the example of FIG. 14). Alternatively or additionally, the conductors 21 that are not shared may all be spaced apart from the shared conductor 20 by the same distance or by two or more different distances.

Providing a plurality of capacitors 18 that comprise one or more shared conductors 20 increases compactness. Alternatively or additionally, fewer components may be needed to manufacture a plurality of capacitors 18 that comprise one or more shared conductors 20.

FIG. 16 illustrates how electrical connections can be made to an example capacitor 18 comprising two parallel conductors 20,21. Terminal 31 allows electrical connection to one of the conductors 20. Terminal 32 allows electrical connection to the other one of the conductors 21.

In an embodiment, the one or more capacitors 18 comprise a capacitor 18 having three or more conductors 20,21. An example of a capacitor 18 having three or more conductors 20,21 is shown in FIG. 17. In this particular example the capacitor 18 has four conductors 20,21. The three or more conductors 20,21 may be mounted such that the vapor can flow through a plurality of gaps 24. At least a subset of the gaps 24 are between different pairs of the conductors 20,21 (as can be seen in the example of FIG. 17).

The provision of three of more conductors 20,21 in a single capacitor 18 makes it possible to provide a high capacitance in a spatially compact form. Providing a high capacitance may improve the accuracy of the measurement of either or both of the concentration of the vapor and the amount of the deposit formed from the vapor. Providing three or more conductors 20,21 may make it possible to provide a larger volume within the gaps 24 for vapor to flow through (while maintaining a spatially compact form). Providing a larger volume within the gaps 24 for vapor to flow through may increase the amount of vapor in the gaps. Increasing the amount of vapor in the gaps may improve the accuracy of the measurement of the concentration of the vapor. Providing three or more conductors may make it possible to provide a greater surface area within the gaps for the deposit from the vapor to form. Providing a greater surface area for the deposit to form may increase the amount of deposit that forms. Increasing the amount of deposit that forms may improve the accuracy of the measurement of the amount of the deposit that forms.

The total volume of the gap 24 and/or the total surface area in the gap 24 available for deposits from the vapor to form may be increased in a capacitor 18 comprising only two conductors 20,21 by increasing the area of the conductors 20,21. However, increasing the area of the conductors 20,21 may decrease the compactness of the capacitor 18 in comparison to a capacitor 18 having the same overall surface area shared between more than two conductors 20,21 (as in FIG. 17 for example).

In an embodiment, the one or more capacitors 18 comprise a first capacitor 18A and a second capacitor 18B. Examples of such an embodiment are shown in FIGS. 18 and 19 and in FIGS. 20 and 21. Each of the first and second capacitors 18A,18B comprises at least two conductors 20,21. The at least two conductors 20,21 of the first capacitor 18A are configured differently from the at least two conductors 20,21 of the second capacitor 18B. The measurement system 12 is configured to use measurements from both of the first capacitor 18A and the second capacitor 18B to distinguish between an effect on the capacitance of the capacitor 18A,18B caused by a concentration of vapor in the gap 24 of the capacitor 18A,18B and an effect on the capacitance of the capacitor 18A,18B caused by an amount of a deposit formed from the vapor in the gap 24 of the capacitor 18A,18B. The measurement system 12 may be configured to distinguish between the effect of the concentration of vapor and the effect of an amount of the deposit for either or both of the first capacitor 18A and the second capacitor 18B. The manner or manners in which the at least two conductors 20,21 of the first capacitor 18A are configured differently from the at least two conductors 20,21 of the second capacitor 18B may be such as to allow distinguishing of these effects to be carried out. The manner or manners in which the at least two conductors 20,21 of the first capacitor 18A are configured differently from the at least two conductors 20,21 of the second capacitor 18B may be such as to allow simultaneous equations to be formed. The simultaneous equations may be solved to determine the concentration of vapor and the amount (e.g. thickness) of the deposit as the two unknowns of the simultaneous equations.

In an embodiment, the first capacitor 18A comprises two conductors 20,21 that face each other over a first surface area. The second capacitor 18B comprises two conductors 20,21 that face each other over a second surface area. As in the example shown in FIGS. 18 and 19, the size of the first surface area may be different from the size of the second surface area. Alternatively or additionally, as in the example shown in FIGS. 20 and 21, an average separation between the two conductors 20,21 of the first capacitor 18A may be different from an average separation between the two conductors 20,21 of the second capacitor 18B.

In an alternative embodiment, the one or more capacitors may comprise a capacitor 18 having at least two conductors 20,21 that are movable relative to each other in order to vary the capacitance of the capacitor 18. A movement mechanism may be provided to drive the relative movement. The movement mechanism may be configured to allow the relative movement to be driven while the radiation source is online. Varying the capacitance of the capacitor 18 may be used to optimise the sensitivity of the measurement of either or both of a concentration of the vapor in the gap 24 of the capacitor 18 and an amount of the deposit in the gap 24 of the capacitor 18. Alternatively or additionally, varying the capacitance of the capacitor 18 may be used to distinguish between an effect on the capacitance of the capacitor 18 caused by a concentration of vapor in the gap 24 of the capacitor 18 and an effect on the capacitance of the capacitor 18 caused by an amount of a deposit formed from the vapor in the gap 24 of the capacitor 18. For example, a first measurement of capacitance may be carried out with the capacitance of the capacitor 18 set to a first value. A second measurement of the capacitance may subsequently be carried out with the capacitance of the capacitor 18 set to a second value (e.g. by moving the conductors 20,21 relative to each other). The two measurements may then be used to form two simultaneous equations that can be solved to determine the concentration of vapor and the amount (e.g. thickness) of the deposit as the two unknowns of the two simultaneous equations.

The capacitance may be varied by moving the conductors 20,21 of the capacitor 18 closer together (thereby increasing the capacitance) or further apart (thereby decreasing the capacitance). Alternatively or additionally, the capacitance may be varied by increasing the surface areas of the conductors 20,21 that are facing each other (thereby increasing the capacitance) or decreasing the surface areas of the conductors 20,21 that are facing each other (thereby decreasing the capacitance).

Figure 22:
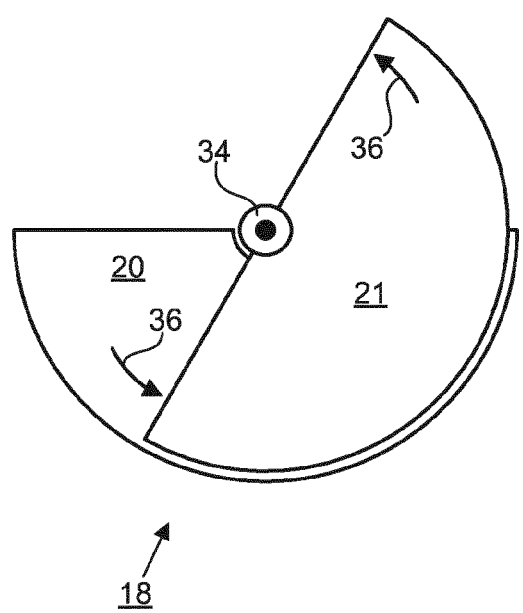
FIG. 22 is a schematic end view of a capacitor having conductors that can move relative to each other in order to vary the capacitance of the capacitor.
Figure 23:
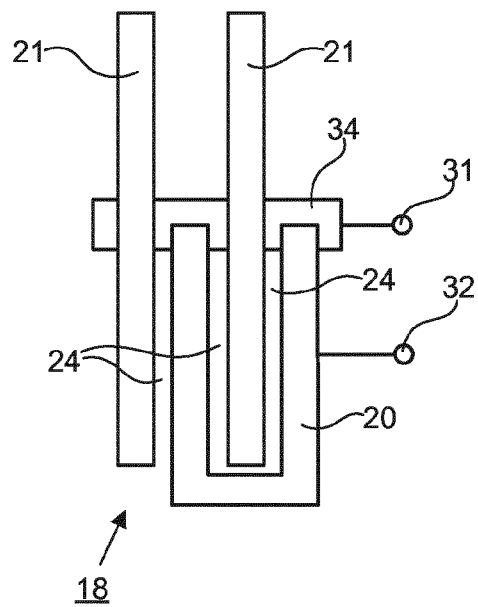
FIG. 23 is a schematic side view of the capacitor of FIG. 22.

In an embodiment, the movement mechanism comprises a rotation mechanism 34. The rotation mechanism is configured to drive relative rotation between two of the conductors 20,21 in order to vary the size of the surfaces areas of the two conductors 20, 21 that face each other. An example arrangement is depicted in FIGS. 22 and 23. FIG. 22 is a schematic end view along an axis of the relative rotation. FIG. 23 is a schematic side view. In the example shown, the conductors 20 are stationary. The conductors 20 may therefore be referred to as a stator. The conductors 21 are mounted so as to be rotatable by the rotation mechanism 34. The conductors 21 may therefore be referred to as a rotor. Arrows 36 show an example direction of rotation. Rotating the conductors 21 in an anticlockwise direction (in the orientation shown in FIG. 22) will decrease the size of the surface areas of the two conductors 20,21 that face each other (thereby decreasing the capacitance). Rotating the conductors 21 in a clockwise direction will increase the size of the surfaces areas of the two conductors 20,21 that face each other (thereby increasing the capacitance).

Figure 24:
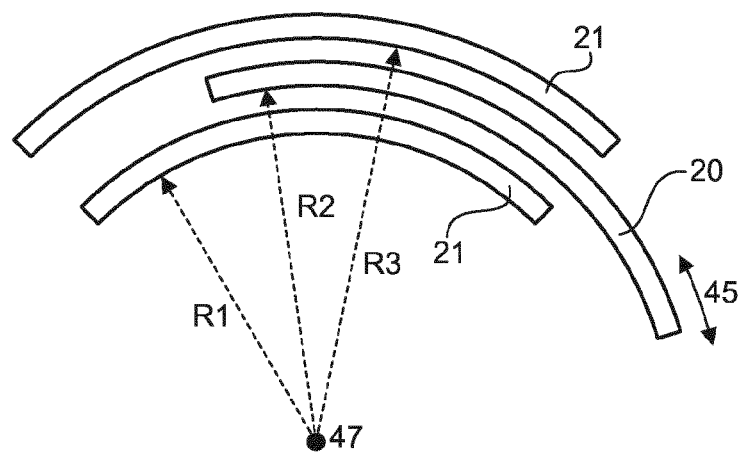
FIG. 24 is a schematic side view of curved conductors that can move relative to each other by rotation of at least one of the conductors.

In an alternative to the arrangement of FIGS. 22 and 23, the capacitor 18 may comprise at least two conductors 20,21 that each comprise a curved portion. An example of conductors according to such an embodiment is shown in FIG. 24. The conductors 20,21 may be moveable relative to each other to cause a change in the sizes of the surfaces areas of the conductors 20,21 that face each other. The curved portions may for example each comprise a portion of a circle when viewed along a first axis 47 (perpendicularly into the page in the orientation shown in FIG. 24). In the particular example of FIG. 24, three conductors 20,21 comprising portions of circles having radii of R1, R2 and R3 are shown. The curved portions may comprise portions of circles that are coaxial with each other about the first axis 47 but which have different radii R1,R2,R3 (as in the example of FIG. 24). Relative rotation of the conductors 20,21 about the first axis 47 may allow the conductors 20,21 to move relative to each other without striking each other. In the example shown in FIG. 24, two capacitors 18 are provided. A first capacitor 18 is formed from the combination of the uppermost conductor 21 and a shared inner conductor 20. A second capacitor 18 is formed from the combination of the lowermost conductor 21 and the shared inner conductor 20. Relative movement (indicated by arrow 45) between the conductors of each of the two capacitors 18 is provided in this example by rotating the shared inner conductor 20 about the first axis 47.

In an embodiment, the one or more capacitors comprises a plurality of capacitors 18 having the same configuration. For example, the plurality of capacitors 18 may comprise conductors of the same shape, size, orientation and/or separation. The plurality of capacitors 18 may have the same capacitance in the absence of any vapor or deposits from the vapor. Providing a plurality of capacitors 18 having the same configuration may reduce errors in the measurement of the concentration of the vapor or the amount of the deposit formed from the vapor. For example, the influence of localized variations in flow, or in other effects that might change the capacitance measurement, may be reduced. Two or more of the plurality of capacitors 18 having the same configuration may be positioned close to each other (which may be particularly appropriate for example where it is desired to reduce the effects of the localized variations). Alternatively or additionally, the plurality of capacitors 18 having the same configuration may be spaced out at a plurality of different positions within the radiation source in order to measure how the concentration of vapor or the amount of deposit varies as a function of position.

In an embodiment, at least one of the one or more capacitors 18 has at least two conductors 20,21 with smooth (e.g. with no surface structure that is visible to the naked eye) opposing faces. Alternatively or additionally, at least one of the one or more capacitors 18 has at least two conductors 20,21 with one or both opposing faces having a surface structure. The surface structure may comprise one or more grooves or other indentations. The surface structure may comprise one or more holes traversing through the conductor. Alternatively or additionally, at least one of the one or more capacitors 18 has at least one conductor having a smooth face and at least one other conductor having a face with a surface structure. The smooth face may or may not be opposite (i.e. opposed to) the face with a surface structure in the case where the capacitor comprises more than two conductors.

The one or more capacitors 18 can be positioned in various locations within the radiation source. The choice of where to provide a capacitor 18 will depend on the particular configuration of the radiation source. It may be desirable to provide capacitors 18 on structures which are particularly prone to build up of deposit due to their location within the radiation source. Some structures may be particularly prone to build up of deposit because they tend to be at a lower temperature than other structures. Condensation of vapor may occur more quickly on structures that are at lower temperature. Alternatively or additionally, some structures may be particularly prone to build up of deposit because of the flow pattern of vapor in the region where the structures are located. For example, regions of relatively stagnant flow may cause different rates of deposit formation than regions where the flow is faster. Alternatively or additionally, it may be desirable to provide capacitors 18 on structures whose performance is likely to be affected more by deposits formed from the vapor. For example, structures having fine channels may become blocked by deposits. For example, a contaminant trap 4230 may comprise a channel structure that may be prone to blocking by deposits. It may therefore be desirable to provide one or more of the capacitors 18 on the contaminant trap (e.g. in the channel structure or behind the channel structure on the opposite side of the channel structure to the plasma 4210).

Figure 25:
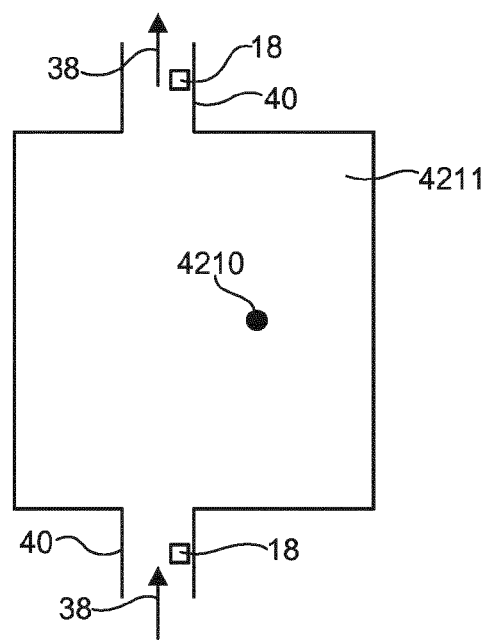
FIG. 25 depicts schematically the positioning of a capacitor in gas delivery channels of a radiation source.

As mentioned above, a gas delivery system 16 may be provided for providing a flow of gas through the radiation source. The gas delivery system 16 may comprise gas delivery channels 40 for inputting gas into the radiation source and for removing gas (and any vapor or other materials conveyed by the gas) from the radiation source (arrows 38). An example of such an arrangement is shown schematically in FIG. 25. Over time, deposits formed from the vapor may build up in the gas delivery channels 40. The build up of deposits in the gas delivery channels may reduce the cross-sectional area of the gas delivery channels 40 and reduce the flow rate of gas through the radiation system. It may therefore be desirable to provide one or more of the capacitors 18 in one or more of the gas delivery channels 40 to allow monitoring of the amount of deposits formed from the vapor in the gas delivery channels 40.

Figure 26:
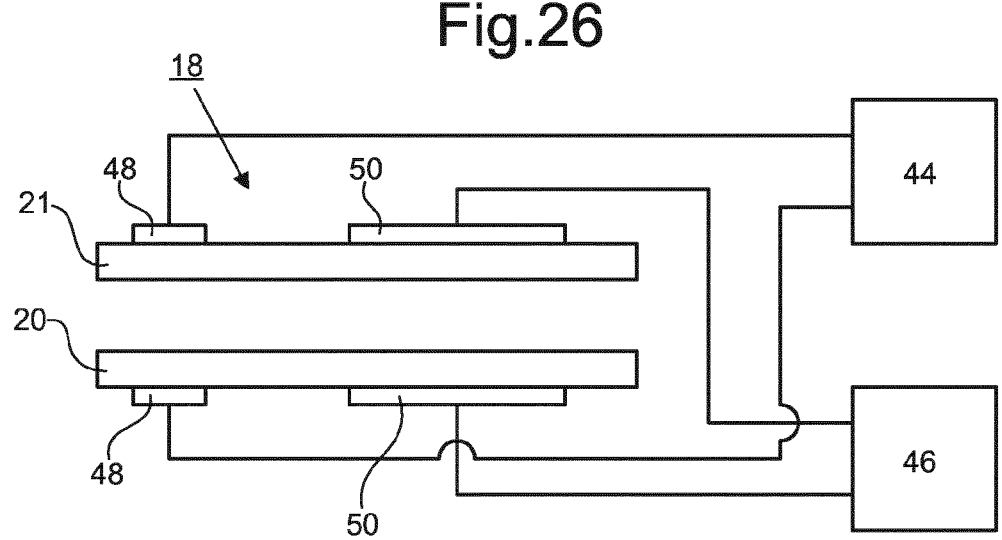
FIG. 26 depicts schematically a temperature measurement system comprising temperature sensors and a heating system comprising heaters.

As mentioned above, condensation of vapor may occur more quickly on structures that are at a lower temperature. It may therefore be desirable to monitor the temperature of one or more of the capacitors 18. Alternatively or additionally, it may be desirable to control the temperature of one or more of the capacitors 18. In any of the embodiments discussed above, and in other embodiments, there may be provided one or both of a temperature measurement system 44 and a heating system 46. An example of such an embodiment is shown in FIG. 26. The temperature measurement system 44 is configured to measure the temperature of one or more of the capacitors 18. The heating system 46 is configured to apply heating selectively to one or more of the capacitors 18. In the embodiment shown, an example capacitor 18 is shown which comprises temperature sensors 48 mounted on the conductors 20,21. The temperature sensors 48 measure the temperature of the conductors 20,21 and output the result of the measurement to the temperature measurement system 44. The temperature measurement system 44 may also receive measurements of the temperature or temperatures from one or more other capacitors 18. In the embodiment shown, the capacitor 18 comprises heaters 50 mounted on the conductors 20,21. The heaters 50 provide heating to the conductors 20,21. The amount of heating may be controlled by the heating system 46. The heating system 46 may therefore control how much heating is applied to the capacitor 18. The heating system 46 may also control how much heating is applied to one or more other capacitors. In the embodiment shown the heaters 50 and temperature sensors 48 are in contact with the conductors 20,21 being heated or sensed. This is not essential. In other embodiments, either or both of the heaters 50 and the temperature sensors 48 may be configured to provide the heating or sensing in a contactless manner.

The temperature measurement system 44 makes it possible to correlate measurements of the concentration of vapor and/or amount of deposit in the gaps of the capacitors 18 with the temperature of the capacitors 18 or the thermal history of the capacitors 18. This information makes it possible to predict with greater accuracy what the thickness of deposit might be on structures within the radiation source. For example, making the temperature or thermal history of a capacitor 18 equal to or similar to the temperature or thermal history of a structure of interest in the radiation source may cause the amount of deposit (e.g. thickness of deposit) formed on the capacitor 18 to be more similar to the amount of deposit formed on the structure of interest. Measuring the amount of deposit on this capacitor 18 may improve the accuracy of a prediction of the amount of deposit formed on the structure of interest.

Additionally or alternatively, the temperature measurement system 44, optionally in combination with the heating system 46, may be used to monitor how the rate of condensation of vapor varies as a function of the temperature of the capacitor 18. Additionally or alternatively, the temperature measurement system 46, optionally in combination with the heating system 46, may be used to monitor how the rate of condensation of the vapor varies as a function of the temperature of the capacitor 18 at different locations in the radiation source. The obtained variation or variations of the rate of condensation with temperature and/or location may be used to modify the radiation source to improve performance, reliability or longevity. For example the temperatures and/or positions of structures within the radiation source may be modified to reduce the speed of condensation on those structures.

Figure 27:
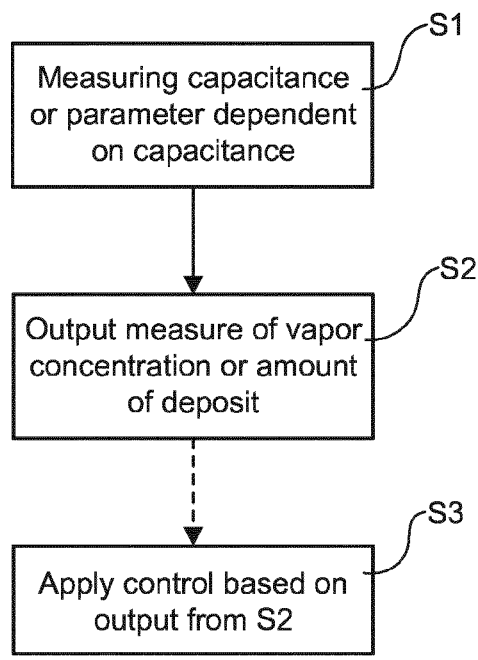
FIG. 27 is a flowchart illustrating example methods of embodiments of the invention.

The above embodiments having been described by reference to apparatus features. The description also encompasses method steps using the apparatus features. An example framework method is illustrated in FIG. 27. According to this framework, there is provided a method of monitoring a radiation source for a lithography apparatus. The radiation source is configured to produce radiation by generating a plasma from a fuel. The method involves use of one or more capacitors 18. Each capacitor 18 comprises at least two conductors 20,21. The conductors 20,21 are mounted such that a vapor can flow through a gap 24 between the conductors 20,21. One or both of a concentration of the vapor in the gap 24 and an amount of a deposit formed from the vapor in the gap 24 has an effect on the capacitance of the capacitor 18. The method comprises a step S1 of measuring a capacitance, or a parameter dependent on the capacitance, of at least one of the one or more capacitors 18 using a measurement system. The method further comprises a step S2 of outputting, for at least one of the one or more capacitors 18, one or both of a measure of a concentration of the vapor in the gap 24 of the capacitor 18 and a measure of an amount of the deposit in the gap 24 of the capacitor 18, using an output from the measurement system. The output of step S2 can be used for monitoring the radiation source without necessarily taking any action in response to the monitoring. Optionally, the method further comprises a step S3 of controlling the radiation source using the output from step S2. For example, the control may be applied using a controller. The control may comprise controlling one or more operating parameters of the radiation source. Optionally, the method of FIG. 27 may be incorporated into a device manufacturing method. The device manufacturing method may comprise using a radiation source to supply radiation to a lithography apparatus. The device manufacturing method may comprise using the lithography apparatus to manufacture a device. The device manufacturing method may comprise controlling the radiation source of the lithography apparatus using the method as described above with reference to FIG. 27.

References to vapor in the above embodiments may be understood to encompass both fuel vapor (e.g. vapor of Sn, Li, Gd or Tb) and vapor of reaction products of the fuel (e.g. stannane), except where expressly stated otherwise.

Although specific reference may be made in this text to the use of lithography apparatus in the manufacture of ICs, it should be understood that the lithography apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. A device for monitoring a radiation source for a lithography apparatus, the radiation source being configured to produce radiation by generating a plasma from a fuel, the device comprising:
   one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor; and
   a measurement system configured to output, for at least one of the one or more capacitors, one or both of a measure of a concentration of the vapor in the gap of the capacitor and a measure of an amount of the deposit in the gap of the capacitor, by measuring a capacitance, or a parameter dependent on the capacitance, of at least one of the one or more capacitors.

2. The device of claim 1, further comprising:
   a controller configured to use the measure of the concentration of the vapor or the measure of the amount of the deposit output by the measurement system to control one or more operating parameters of the radiation source.

3. The device of claim 2, wherein the one or more operating parameters comprise operating parameters of a laser delivery system that is configured to deliver laser radiation to the fuel in order to create the plasma.

4. The device of claim 2, wherein the one or more operating parameters comprise operating parameters of a fuel delivery system that is configured to generate a flow of the fuel to be vaporized.

5. The device of claim 2, wherein the controller is configured to control the one or more operating parameters so that a rate of generation of the plasma is increased when the measure of the concentration of the vapor measured by the measurement system falls below a lower threshold value.

6. The device of claim 2, wherein the one or more operating parameters comprise operating parameters of a gas delivery system configured to provide a flow of gas through the radiation source for removing vapor from the radiation source.

7. The device of claim 2, wherein the controller is configured to detect when the measure of the amount of the deposit measured by the measurement system rises above an upper threshold value.

8. The device of claim 7, wherein the controller is further configured to output an alarm signal indicating that the measure of the amount of the deposit measured by the measurement system has risen above the upper threshold value, initiate a cleaning procedure, or cause the radiation source to enter a safety mode or to shut down.

9. The device of claim 1, wherein
   the one or more capacitors comprise a first capacitor and a second capacitor, each of the first and second capacitors comprising at least two conductors;
   the at least two conductors of the first capacitor are configured differently from the at least two conductors of the second capacitor; and
   the measurement system is configured to use measurements from both of the first capacitor and the second capacitor to distinguish, for either or both of the first capacitor and the second capacitor, between an effect on the capacitance of the capacitor caused by a concentration of vapor in the gap of the capacitor and an effect on the capacitance of the capacitor caused by an amount of a deposit formed from the vapor in the gap of the capacitor.

10. The device of claim 9, wherein
    the first capacitor comprises two conductors that face each other over a first surface area;
    the second capacitor comprises two conductors that face each other over a second surface area; and
    the size of the first surface area is different from the size of the second surface area.

11. The device of claim 9, wherein
    the first capacitor comprises two conductors that face each other;
    the second capacitor comprises two conductors that face each other; and
    an average separation between the two conductors of the first capacitor is different from an average separation between the two conductors of the second capacitor.

12. The device of claim 1, wherein the one or more capacitors comprise a capacitor having at least two conductors that are parallel plates.

13. The device of claim 1, wherein the one or more capacitors comprise a capacitor having at least two conductors and a movement mechanism configured to provide relative movement between the conductors in order to vary the capacitance of the capacitor.

14. The device of claim 13, wherein the movement mechanism comprises a rotation mechanism configured to provide relative rotation between two of the conductors in order to vary the size of the surface areas of the two conductors that face each other.

15. The device of claim 1, wherein the one or more capacitors comprise a capacitor having three or more conductors mounted such that the vapor can flow through a plurality of gaps, each of the plurality of gaps being provided between different pairs of the conductors.

16. The device of claim 1, wherein the fuel comprises Li, Sn, Gd or Tb.

17. The device of claim 1, further comprising one or both of a temperature measurement system configured to measure the temperature of one or more of the capacitors and a heating system configured to apply heating to one or more of the capacitors.

18. A radiation source comprising the device for monitoring the radiation source for a lithography apparatus, the radiation source being configured to produce radiation by generating a plasma from a fuel, the device comprising:
one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor; and
a measurement system configured to output, for at least one of the one or more capacitors, one or both of a measure of a concentration of the vapor in the gap of the capacitor and a measure of an amount of the deposit in the gap of the capacitor, by measuring a capacitance, or a parameter dependent on the capacitance, of at least one of the one or more capacitors.

19. A method of monitoring a radiation source for a lithography apparatus, the radiation source being configured to produce radiation by generating a plasma from a fuel, the method comprising:
providing one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor; and
measuring a capacitance, or a parameter dependent on the capacitance, of at least one of the one or more capacitors and using the measured capacitance or parameter to provide an output comprising one or both of a measure of a concentration of the vapor in the gap of the capacitor and a measure of an amount of the deposit in the gap of the capacitor.

20. A device manufacturing method, comprising:
using a radiation source to supply radiation to a lithography apparatus;
using the lithography apparatus to manufacture a device; and
controlling the radiation source by:
providing one or more capacitors, wherein each capacitor comprises at least two conductors that are mounted such that a vapor can flow through a gap between the conductors, wherein one or both of a concentration of the vapor in the gap and an amount of a deposit formed in the gap from the vapor has an effect on the capacitance of the capacitor;
measuring a capacitance, or a parameter dependent on the capacitance, of at least one of the one or more capacitors and using the measured capacitance or parameter to provide an output comprising one or both of a measure of a concentration of the vapor in the gap of the capacitor and a measure of an amount of the deposit in the gap of the capacitor; and
using a controller to control one or more operating parameters of the radiation source using the output.

* * * * *